United States Patent
Cook et al.

(10) Patent No.: US 7,135,024 B2
(45) Date of Patent: Nov. 14, 2006

(54) LUMBAR SPINE FIXATION DEVICE

(75) Inventors: Daniel J. Cook, Richmond Heights, MO (US); Daniel Scodary, St. Louis, MO (US)

(73) Assignee: Cookgas, L.L.C., St. Louis, MO (US)

( * ) Notice: Subject to any disclaimer, the term of this patent is extended or adjusted under 35 U.S.C. 154(b) by 587 days.

(21) Appl. No.: 10/607,355

(22) Filed: Jun. 26, 2003

(65) Prior Publication Data

US 2004/0010254 A1  Jan. 15, 2004

Related U.S. Application Data

(63) Continuation-in-part of application No. 09/390,607, filed on Sep. 3, 1999, now abandoned.

(51) Int. Cl.
*A61B 17/58* (2006.01)
(52) U.S. Cl. ............................................. 606/69
(58) Field of Classification Search ............... 606/61, 606/69, 70, 71, 72, 73, 86, 96, 99, 104; 623/17.11–17.16
See application file for complete search history.

(56) References Cited

U.S. PATENT DOCUMENTS

| | | | |
|---|---|---|---|
| 4,338,926 A | | 7/1982 | Kummer et al. |
| 4,794,918 A | | 1/1989 | Wolter |
| 4,955,908 A | * | 9/1990 | Frey et al. ............... 623/17.16 |
| 5,015,247 A | | 5/1991 | Michaelson |
| 5,085,660 A | | 2/1992 | Lin |
| 5,234,431 A | | 8/1993 | Keller |
| 5,246,458 A | * | 9/1993 | Graham .................... 623/17.14 |
| 5,366,455 A | | 11/1994 | Dove et al. |
| 5,423,826 A | | 6/1995 | Coates et al. |
| 5,484,437 A | * | 1/1996 | Michelson ................ 606/61 |
| 5,534,031 A | * | 7/1996 | Matsuzaki et al. ........ 623/17.11 |
| 5,766,254 A | | 6/1998 | Gelbard |
| 5,797,909 A | | 8/1998 | Michaelson |
| 5,899,908 A | * | 5/1999 | Kuslich et al. ............... 606/96 |
| 5,947,968 A | | 9/1999 | Rogozinski |
| 6,045,552 A | | 4/2000 | Zucherman et al. |
| 6,066,142 A | * | 5/2000 | Serbousek et al. ............ 606/96 |
| 6,066,175 A | * | 5/2000 | Henderson et al. ...... 623/17.11 |
| 6,120,503 A | | 9/2000 | Michelson |
| 6,156,037 A | | 12/2000 | LeHuec et al. |
| 6,183,478 B1 | | 2/2001 | Konieczynski |
| 6,193,721 B1 | * | 2/2001 | Michelson .................... 606/70 |
| 6,228,085 B1 | * | 5/2001 | Theken et al. ................ 606/61 |
| 6,235,059 B1 | * | 5/2001 | Benezech et al. ......... 623/17.16 |
| 6,402,756 B1 | | 6/2002 | Ralph et al. |
| 6,413,259 B1 | | 7/2002 | Lyons et al. |
| 2001/0020185 A1 | * | 9/2001 | Ray ........................ 623/17.11 |
| 2002/0107519 A1 | | 8/2002 | Dixon et al. |
| 2002/0128652 A1 | * | 9/2002 | Ferree ......................... 606/61 |
| 2002/0198533 A1 | | 12/2002 | Geisler et al. |

* cited by examiner

*Primary Examiner*—Eduardo C. Robert
*Assistant Examiner*—Nicholas Woodall
(74) *Attorney, Agent, or Firm*—Lewis, Rice & Fingersh, L.C.

(57) ABSTRACT

A spine fixation device is described that includes an alignment plate having top and bottom surfaces for temporary attachment to a pair of adjacent vertebrae on a body, at least two surgical screws, and at least one spacer. The alignment plate is adapted not to move transversely with respect to the longitudinal axis of the spine. The plate includes at least two openings spaced from each other a distance such that at least two of the openings open onto adjacent vertebrae, and has a predetermined angle formed therein so as to position adjacent vertebrae at a predetermined angle. The adjacent vertebrae are thus fixedly secured at the predetermined angle by the plate.

1 Claim, 4 Drawing Sheets

LUMBAR SPINE FIXATION DEVICE

CROSS REFERENCE TO RELATED APPLICATION

This is a continuation in part of U.S. patent application Ser. No. 09/390,607, filed Sep. 3, 1999 and now abandoned.

STATEMENT REGARDING FEDERALLY-SPONSORED RESEARCH AND DEVELOPMENT

Not applicable.

REFERENCE TO MICROFICHE APPENDIX

Not applicable:

BACKGROUND OF THE INVENTION

This invention relates generally to the field of surgical devices and methods of fixing adjacent vertebrae in the spine. More specifically, the present invention is a device, and a method of using such, which fixes adjacent vertebrae together to prevent movement of the vertebrae with respect to each other. The device may be used during surgical operations or as and implant for permanent spinal fixation.

The history and art surrounding surgical articles and methods to aid in the fusion of adjacent vertebrae is aptly chronicled in U.S. Pat. No. 5,797,909 to Michaelson. Although a recap of that history is not necessary here, an understanding of the Michaelson apparatus and method is necessary to appreciate the present invention.

The Michaelson apparatus and method are believed to represent the current state of the art in temporary fixation of adjacent vertebrae during surgical procedures. As such the Michaelson invention appears to be widely used for spinal fusion operations. Essentially, the primary embodiment of the Michaelson apparatus is a hollow sleeve with teeth at one end. When used in surgeries from the anterior aspect of a patient, the sleeve is driven into adjacent vertebrae over the anterior aspect of the intervertebral space between the vertebrae, which are to be fused. The teeth, when driven into the adjacent vertebrae, work to help stabilize the anterior portions of the two vertebrae and the intervertebral space during the various drilling and surgical operations taking place through the hollow sleeve and within the intervertebral space.

In use, however, the teeth may allow some unwanted relative movement of the vertebrae because they do not stabilize both the anterior and posterior aspects of the vertebrae. This is especially a concern during drilling operations where creating holes with parallel sides in the intervertebral space and the adjacent vertebrae end planes is crucial. For example, when the known apparatus is attached to the anterior aspect of the adjacent vertebrae and drilling is commenced in the intervertebral space from the anterior aspect towards the posterior aspect, the force of the drill may cause a vertebral end plate of the adjacent vertebrae to separate at the posterior aspect of the vertebrae. Because of this movement, the side of the hole drilled in the vertebra and end plates will taper and will not be parallel when the drill is removed from the hole.

It is believed that this tapering of the walls of the drilled hole can be significant and detrimental. This degree of inaccuracy may lead to misalignment of the fused vertebrae, as well as the exertion of excessive pressure on parts of the implant plug inserted into the hole to fuse the vertebrae. This later consequence is of particular concern where a relatively fragile bone cage plug is used because the irregular pressures can damage the plug. By fixing the adjacent vertebrae in all relative planes the present invention provides for the complete relative stabilization of the adjacent vertebrae, thus ensuring accuracy and precision of surgical procedures performed on the vertebrae. The present invention may also be used as a vertebral implant, permanently stabilized adjacent vertebrae after a surgical procedure, or as a means of correcting a problem with a patient's spine.

BRIEF DESCRIPTION OF THE INVENTION

The invention is a spine fixation device for application to the spine of a patient that includes a plate, having top and bottom surfaces for attachment to a pair of adjacent vertebrae on a human body, the plate having at least two openings, each being spaced from each other a distance such that at least two of the openings open onto adjacent vertebrae. The plate has a predetermined angle formed therein so as to position adjacent vertebrae at a predetermined angle, a spacer on its bottom surface, which has a predetermined length as measured along the longitude axis of the plate, wherein the predetermined length is equal to the desired space between the adjacent vertebrae, wherein the spacer is oriented on the bottom surface of the plate such that when the plate is installed on the adjacent vertebrae, the spacer is between the adjacent vertebrae in the intervertebral space. The spine fixation device also includes at least two surgical screws that are adapted to pass through the openings in the plate and to screw into the adjacent vertebrae.

In the method aspect, the invention consists of a procedure to fix the spine comprising multiple steps. The physician, using the angle of the plate and central spacer to assure optimal positioning of vertebrae with respect to each other, attaches a plate with spacer to a pair of adjacent vertebrae. The surgical screws are installed through the plate into adjacent vertebrae to lock the vertebrae and plate together so as to position the adjacent vertebrae at the predetermined angle and position. The spacer or plate then becomes a support over which a single or double lumen guide tube sleeve is placed, the spacer sliding between the two barrels of a double lumen guide tube or to the side of the single tube assuring that the tube lumen guide is perfectly placed between the two vertebrae while preventing lateral translation of the guide tube during the drilling process. At least one hole is then drilled into or between the adjacent vertebrae on each side of the plate, the plate holding the adjacent vertebrae at the predetermined angle while the holes are being drilled. Finally, an implant is placed through the hollow sleeve and into the intervertebral space permanently fixing the adjacent vertebrae securely at the predetermined angle and position. The plate then can be or left in place for further stabilization if desired.

Other objects and features will be in part apparent and in part pointed out herein after.

BRIEF DESCRIPTION OF THE DRAWINGS

Similar reference characters indicate similar parts throughout the several views of the drawings.

DETAILED DESCRIPTION OF THE INVENTION AND MODES FOR CARRYING OUT THE INVENTION

Figure 1:
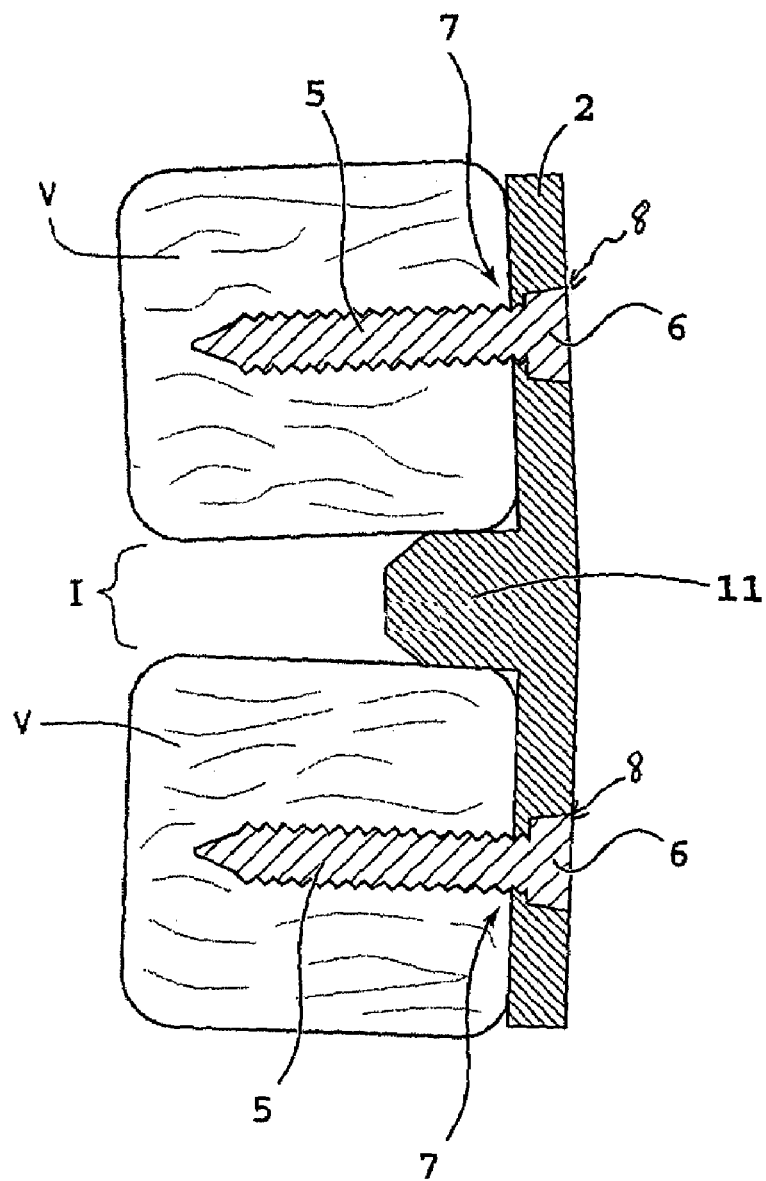
FIG. 1 is a side view of the inventive apparatus installed on the anterior aspects of adjacent vertebrae.
Figure 2:
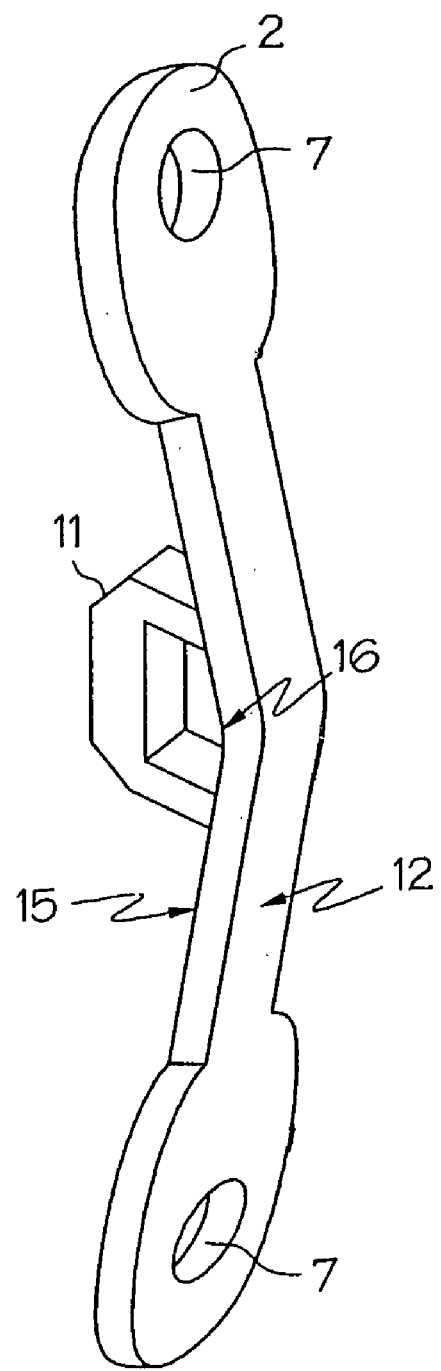
FIG. 2 is a top view of an embodiment of the plate having two openings.

Turning to FIG. 1, we see a cross-section of the inventive apparatus 1 disposed on the adjacent vertebrae V over an intervertebral space I. The apparatus comprises an alignment plate 2 having at least two openings 7 therethrough, at least one spacer 11 on the bottom surface of alignment plate 2, and at least two surgical screws 5 having a flange 6 thereon. Spacers 11 are self-centering longitudinally with respect to the spine. Spacers 11 are sized to fit within intervertebral space I. As shown in FIG. 2, alignment plate 2 has a top surface 12, a bottom surface 15, as well as a predetermined angle 16 formed between the ends of the alignment plate 2. The openings 7 are spaced from each other such that when alignment plate 2 is affixed to adjacent vertebrae V, each of openings 7 open onto different vertebrae V.

In one embodiment of the invention, alignment plate 2 comprises at least two indentations 8 within the top surface 12 of alignment plate 2 above openings 7. The indentations 8 are for receiving surgical screws 5, and more particularly flanges 6 of surgical screws 5. Accordingly, when screws 5 are screwed into adjacent vertebrae V through openings 7, flange 6 rests within the top surface 12 of alignment plate 2.

In one optional embodiment, the apparatus of the invention comprises a fixation plate (not shown). Use of fixation plate is not critical to the operation of the inventive apparatus 1, acting only as an additional stabilizer. In embodiments comprising a fixation plate, the fixation plate is secured to the apparatus of the invention by placing in onto alignment plate 2 with the distal ends of screws passing through openings 7 in the fixation plate and alignment plate 2 and by tightening nuts onto screws 5. The openings in the fixation plate may, if desired, be sized such that their longitudinal dimension is greater than the diameter of screws 5. In this way, the fixation plate may be moved longitudinally with respect to alignment plate 2. Like alignment plate 2, the fixation plate also has a predetermined angle formed therein, which substantially corresponds to the angle 16 in alignment plate 2 and the angle between the now fixed adjacent vertebrae V.

To ensure effective use of the apparatus of the invention 1, a surgical kit for use of the invention may contain alignment plates 2 of various sizes, varying angles 16 and with various sizes of spacers 11.

As shown in FIGS. 1 and 2, angle 16 of alignment plate 2 ensures proper alignment of vertebrae V once mounted. Similarly, the self-centering spacer 11 extends into intervertebral space I and ensures that proper spacing between vertebrae V is achieved and maintained as the apparatus of the invention 1 is mounted. The self-centering nature of spacer 11 ensures that alignment plate 2 is properly centered over intervertebral space I. Given the natural variances of spinal geometry due to differently sized patients and other factors, spacer 11 may come in various sizes and shapes.

Figure 3:
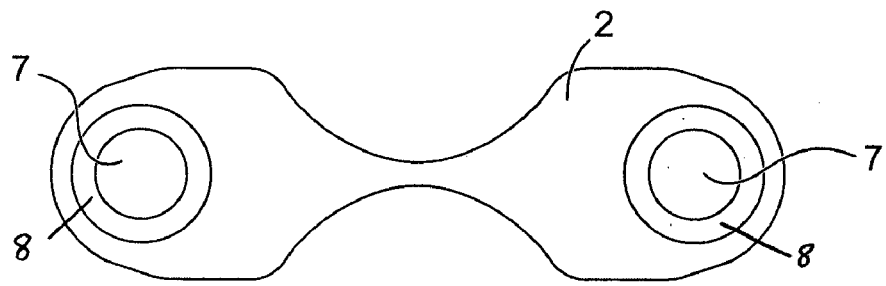
FIG. 3 is a top view of an embodiment of the plate having two openings.
Figure 4:
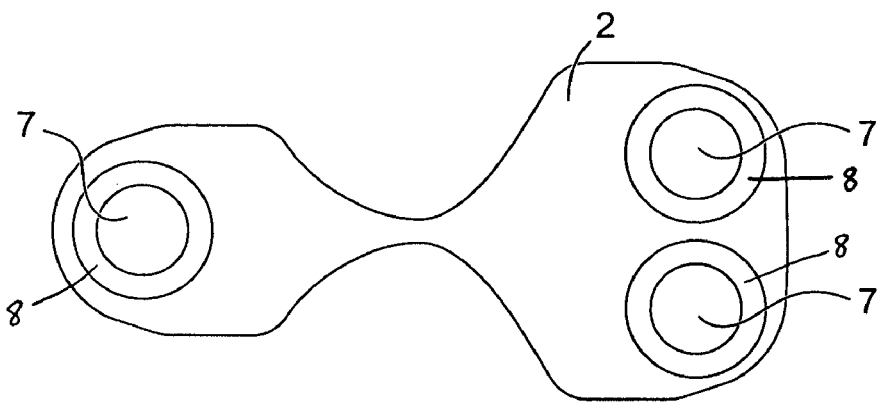
FIG. 4 is a top view of an embodiment of the plate having three openings.
Figure 5:
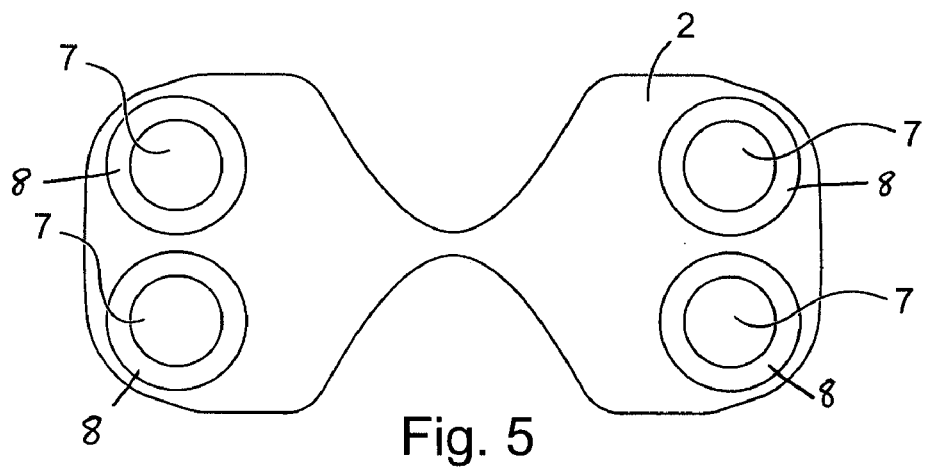
FIG. 5 is a top view of an embodiment of the plate having four openings.

Openings 7 of alignment plate 2 are sized to receive surgical screws 5. With reference to FIGS. 3–5, alignment plate 2 comprises at least two openings 7 spaced from each other distance such that openings 7 open onto adjacent vertebrae V. Alignment plate 2 may comprise any number of openings 7 depending on the specific nature of the procedure during which the inventive apparatus 1 is employed. In one embodiment, alignment plate 2 comprises two openings 7 that are spaced apart a distance such that each open onto adjacent vertebrae V. In another embodiment, alignment plate 2 comprises three openings 7 that are spaced apart a distance such that two openings 7 open onto one vertebrae V and the third opening 7 opens onto an adjacent vertebrae V. In yet another embodiment of the invention, alignment plate 2 comprises four openings 7 that are spaced apart a distance such that two openings 7 open onto one vertebrae V, and two openings 7 open onto an adjacent vertebrae V.

Screws 5 may optionally contain a flange 6, the diameter of which is larger than the openings 7. In one embodiment, the flange 6 rests within, the top surface 12 of alignment plate 2 within indentions 8. Accordingly, when screws 5 are screwed into adjacent vertebrae V through openings 7 in alignment plate 2, flange 6 rests in indentions 8 within the top surface of alignment plate 2. As a result, when the proximal ends of screws 5 are passed through openings 7, screws 5 rest within the top surface 12 of alignment plate 2. Thus, screws 5 hold alignment plate 2 firmly to vertebrae V. In an alternative embodiment, alignment plate 2 does not comprise indentation 8, and flange 6 rests on the top surface of 12 of alignment plate 2. Accordingly, as the proximal ends of screws 5 are passed through openings 7, progress of screws 5 through alignment plate 2 is stopped by the contact of flange 6 with the top surface 12 of alignment plate 2.

In the method aspect, the invention comprises attaching alignment plate 2 to a pair of adjacent vertebrae V on a patient's body, and fixing alignment plate 2 from moving transversely with respect to the longitudinal axis of alignment plate 2 and the spine of the patient by placing a pair of surgical screws 5 placed through openings 7 within alignment plate 2, and into adjacent vertebrae V so as to position adjacent vertebrae V at a predetermined angle 16 with respect to each other. The optimal vertebral spacing is predetermined based on the longitudinal length of the spine attached to alignment plate 2. A hollow single or double lumen sleeve may then be placed in operative contact with plate 2 using the plate 2 as a guide for the hollow sleeve to guide in drilling holes for implant cages between the vertebrae. A spinal fixation implant is then placed through the hollow sleeve and into intervertebral space V. The spinal fixation implant may be any implant used to fix the spine, including a fusion implant.

Figure 6:
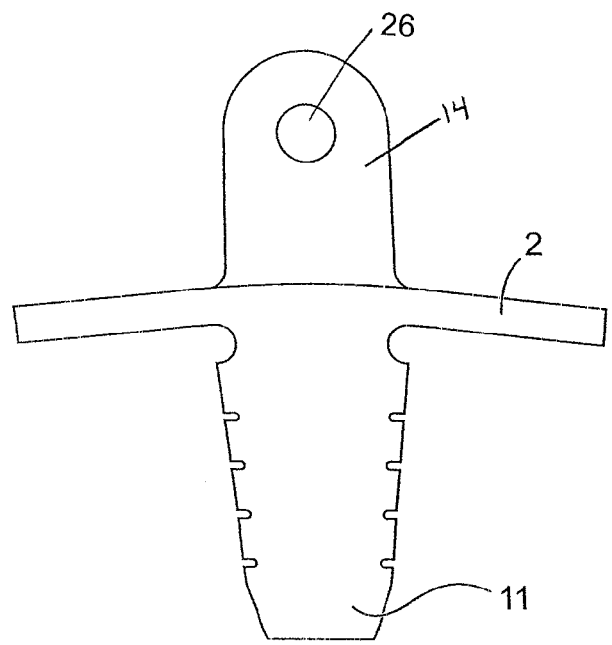
FIG. 6 is a side view of an embodiment of the plate having an extension member thereon.
Figure 7:
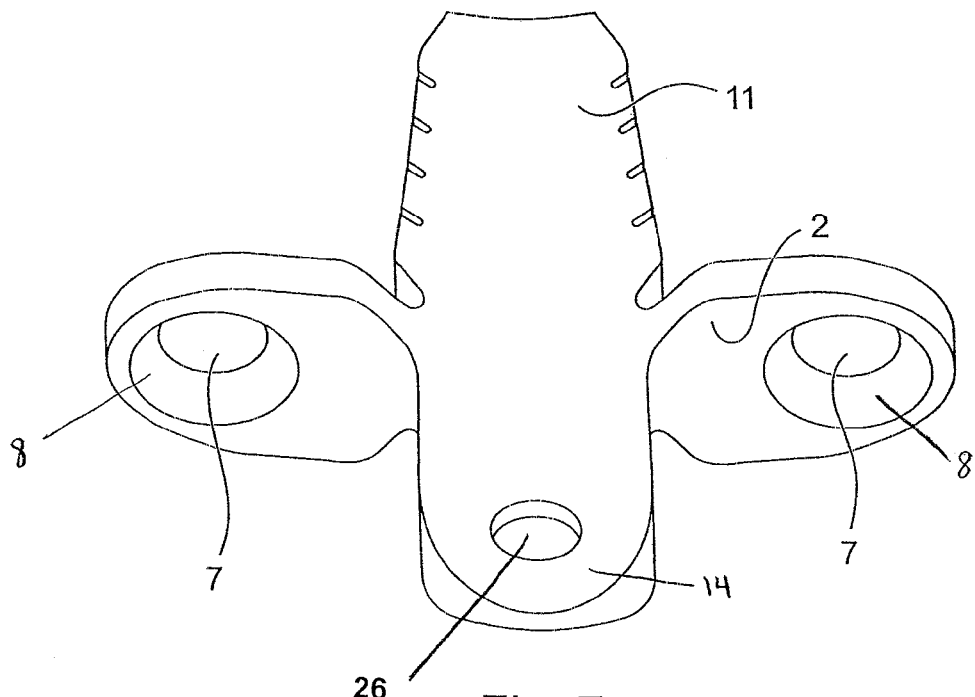
FIG. 7 is a perspective view of the inventive apparatus having an extension member thereon.

As shown in FIGS. 6 and 7, alignment plate 2 may optionally comprise an extension member 14 disposed on the top surface 12 of alignment plate 2. Extension member 14 acts as a mechanism for handling alignment plate 2. Extension member 14 may be used to transport and mount alignment plate 2. Extension member 14 may also be used to remove alignment plate 2 during, or after a surgical procedure. Although not illustrated herein, extension member 14 may be placed anywhere on the top surface 12 of alignment plate 2. preferably, however, extension member 14 is centered with respect to the ends of alignment plate 2. Extension member 14 may comprise at least one opening 26 to facilitate handling of the inventive apparatus 1, as well as other features like ridges for gripping.

In view of the above, it will be seen that the several objects of invention are achieved and other advantages are obtained. Various changes can be made in the above construction without departing from the scope of the invention. It is intended that all matter contained in the above description shall be interpreted as illustrative and not limiting.

What is claimed:

1. A method of fixing the spine, comprising the steps of:
  attaching an alignment plate to a pair of adjacent vertebrae on a body;
  placing a pair of surgical screws through the alignment plate into adjacent vertebrae so as to position adjacent vertebrae at a predetermined angle with respect to each other;
  drilling at least one hole into or between the adjacent vertebrae on each side of the alignment plate, said alignment plate holding the adjacent vertebrae at the predetermined angle while the holes are being drilled;
  placing a hollow sleeve in operative contact with the alignment plate and using the hollow sleeve to guide the drilling; and
  placing a spinal fixation implant through the hollow sleeve and into the intervertebral space.

* * * * *